(12) United States Patent
Otjes et al.

(10) Patent No.: US 10,274,457 B2
(45) Date of Patent: Apr. 30, 2019

(54) GAS COMPONENT CONCENTRATION MEASUREMENT DEVICE AND METHOD FOR GAS COMPONENT CONCENTRATION MEASUREMENT

(71) Applicant: STICHTING ENERGIEONDERZOEK CENTRUM NEDERLAND, Petten (NL)

(72) Inventors: Rene Paul Otjes, Petten (NL); Robbert Rodink, Petten (NL)

(73) Assignee: STICHTING ENERGIEONDERZOEK CENTRUM NEDERLAND, Petten (NL)

( * ) Notice: Subject to any disclaimer, the term of this patent is extended or adjusted under 35 U.S.C. 154(b) by 345 days.

(21) Appl. No.: 15/309,681

(22) PCT Filed: May 7, 2015

(86) PCT No.: PCT/NL2015/050314
§ 371 (c)(1),
(2) Date: Nov. 8, 2016

(87) PCT Pub. No.: WO2015/170980
PCT Pub. Date: Nov. 12, 2015

(65) Prior Publication Data
US 2017/0176378 A1 Jun. 22, 2017

(30) Foreign Application Priority Data
May 9, 2014 (NL) ...................................... 2012788

(51) Int. Cl.
*G01N 7/00* (2006.01)
*G01N 27/416* (2006.01)
(Continued)

(52) U.S. Cl.
CPC ......... *G01N 27/416* (2013.01); *G01N 1/2214* (2013.01); *G01N 33/004* (2013.01);
(Continued)

(58) Field of Classification Search
CPC ............... G01N 27/416; G01N 1/2214; G01N 33/0042; G01N 33/0037; G01N 33/004;
(Continued)

(56) References Cited

U.S. PATENT DOCUMENTS 3,620,931 A 11/1971 Reichner
4,030,887 A 6/1977 Poli et al.
(Continued)

FOREIGN PATENT DOCUMENTS

DE 38 09 082 A1 10/1988
GB 1 238 910 A 7/1971
WO 00/42427 A1 7/2000

OTHER PUBLICATIONS

International Search Report, dated Aug. 27, 2015, from corresponding PCT Application.

*Primary Examiner* — Dennis White
(74) *Attorney, Agent, or Firm* — Young & Thompson

(57) ABSTRACT

A measuring device for measuring a concentration of a gas component in a gas includes a flow generating device, a first conduit, a second conduit, and an electrochemical detector configured for sensing the gas component concentration in the gas. The first and second conduits are arranged in parallel, and the flow generating device is connected with an inlet of the first conduit and an inlet of the second conduit. The flow generating device is arranged for generating a gas flow in each of the conduits. The measuring device is arranged to alternately couple either an outlet of the first conduit or an outlet of the second conduit to an inlet of the
(Continued)

detector, wherein the first conduit is provided with a reactant for absorbing or stripping the gas component.

20 Claims, 3 Drawing Sheets

(51) Int. Cl.
*G01N 33/00* (2006.01)
*G01N 1/22* (2006.01)

(52) U.S. Cl.
CPC ..... *G01N 33/0024* (2013.01); *G01N 33/0037* (2013.01); *G01N 33/0042* (2013.01); *G01N 33/006* (2013.01); *Y02A 50/245* (2018.01)

(58) Field of Classification Search
CPC . G01N 33/0024; G01N 33/006; Y02A 50/245
See application file for complete search history.

(56) References Cited

U.S. PATENT DOCUMENTS

| | | |
|---|---|---|
| 4,141,689 A | 2/1979 | Bergman |
| 2004/0112117 A1 | 6/2004 | Wright et al. |
| 2011/0156715 A1 | 6/2011 | Groves |

GAS COMPONENT CONCENTRATION MEASUREMENT DEVICE AND METHOD FOR GAS COMPONENT CONCENTRATION MEASUREMENT

FIELD OF THE INVENTION

The present invention relates to a gas component concentration measurement device for measuring concentrations of a gas component in a gas such as ambient air. Additionally, the invention relates to a method for measuring such concentrations.

BACKGROUND

To improve environmental quality for living beings, exposure to polluting substances is an issue. Typically, for polluting substances maximum exposure concentrations have been established.

In ambient air, substances such as NO (nitrogen monoxide), NO2 (nitrogen dioxide), SO2 (sulphur dioxide), CO (carbon monoxide) are considered as polluting and posing a health risk to living beings or serve as indicator for other types of pollutants.

To monitor these substances various methods exist.

For example, for NO2 monitoring and measurement, passive sampling is known. This sampling method involves exposing a diffusion tube comprising a NO2 absorbing reactant to ambient air for a predetermined time. During exposure the NO2 absorbing reactant absorbs NO2, which creates reaction products in the reactant. After exposure the NO2 absorbing reactant is analyzed to determine presence and amount of the reaction products as a measure for the concentration of NO2 during the exposure. A well known type of a passive sampler is the Palmes tube which is based on triethanolamine (TEA) as NO2 absorber.

Passive sampling may involve low costs, but the method is relatively time consuming and has long integration times.

Also, real time monitoring devices are commercially available that are based on electrochemical cells. Such cells comprise electrode and counter electrode pairs in which the electrode and counter electrode are separated by an electrolyte-based medium. Presence of the targeted polluting substance in the electrochemical cell will influence the electrochemical potential in the electrochemical cell. The electrochemical potential is typically proportional to the concentration of the targeted polluting substance.

Use of electrochemical cells in monitoring polluting substances allows in principle for (almost) real time detection and analysis. However, electrochemical cells of this type are known to be sensitive to variations of the humidity of the gas volume being analyzed. Additionally, the sensitivity for a particular gas species may be affected by other interfering gas species in the measured gas volume (cross-sensitivity). Such cross-sensitivity may vary as a function of concentration of the interfering gas species and the combinations of these species. Both humidity and cross-sensitivity effects are adverse to the reproducibility of measurements by thus type of electrochemical cell devices.

To reduce the cross-sensitivity, additional correction by computational models is available. The computational models are based on measurements of the interfering gas species (and combinations thereof) that typically suffer from a similar cross-sensitivity effect. This type of correction is computationally intensive and adds largely to the costs of this type of device.

It is an object of the present invention to overcome or mitigate the disadvantages of the prior art.

SUMMARY OF THE INVENTION

The object of the invention is achieved by a measuring device for measuring a level of a gas component in a gas comprising a gas pump, a first flow chamber, a second flow chamber, a selecting valve and an electrochemical detector configured for sensing the gas component level in the gas and for generating an electrical sensing signal corresponding with the gas component level; the gas pump having an inlet for receiving gas; the gas pump being connected through a first outlet channel to an inlet of the first flow chamber; the gas pump being connected through a second outlet channel to an inlet of the second flow chamber, in such a manner that in use a first gas flow in the first flow chamber is parallel to a second gas flow in the second flow chamber; an outlet of the first flow chamber being connected to a first inlet of the selecting valve; an outlet of the second flow chamber being connected to a second inlet of the selecting valve; the selecting valve being connected through an outlet to an inlet of the detector; the selecting valve being configured to alternately connect one of the respective outlets of the first and second flow chambers to the inlet of the detector, wherein the first flow chamber is provided with an absorber substance for selectively absorbing said gas component, and wherein the measuring device comprises an absorbent for moisture which does not absorb the gas component, the absorbent for moisture being arranged downstream of the first and second flow chambers in a flow chamber downstream from the selecting valve and upstream from the detector in the measuring device, wherein the absorbent for moisture is arranged for dampening variation of moisture in the gas which was taken in by gas pump.

The gas pump is for example a fan or a flow generating device, creates gas flows in the first and second parallel flow chambers or conduits. In the first chamber a reactant that absorbs or strips the targeted gas component is arranged. In an embodiment, the flow chambers comprise a space in which a cartridge holding the reactant is positioned.

By the reactant in the first chamber, the targeted gas component is removed from the gas flow through the first flow chamber, while the gas flow through the second flow chamber is not affected.

By alternately coupling the gas flow from the first flow chamber, i.e., the gas flow without the targeted gas component, or the other gas flow through the second flow chamber which contains an amount of the targeted gas, the detector is alternately exposed to a gas flow with or without the targeted gas component.

The other components in the gas flows will be substantially the same, since these components are not affected by the reactant.

Thus, the detector will observe a variation of the sensing signal that varies with the switching between the gas flow with the targeted gas component and the gas flow without the targeted component. As a result the variation of the sensing signal will be proportional with the presence of the targeted gas component.

According to the invention, the absorbent for moisture which does not absorb the gas component, is arranged downstream of the first and second flow chambers in a further flow chamber downstream from the selecting valve and upstream from the detector in the measuring device, and dampens variation of moisture in the gas which was taken in by gas pump. Also, the provision of a moisture adsorbent delays moisture from the first and second gas flows. By affecting the moisture concentration a base line drift of the detector is reduced and the accuracy of the detector improved.

Moreover by its arrangement downstream of the reactant, the adsorbent for moisture provides to dampen the variation in humidity to much larger time domains (on a time scale of one or more hours) than the switching frequency of the valve (on a time scale of minutes). Therefore variations in the humidity (due to TEA affinity with humidity and changing ambient air humidity conditions) do not interfere with the differential measurement technique.

In an embodiment, the variation is determined by measurement of the difference of the detector signals between an exposure to the gas flow with the targeted gas component and an exposure to the gas flow without the targeted gas component.

According to an aspect, the invention also relates to a measuring device as described above, further comprising control means for control of the selecting valve to switch between the connection of one of the respective outlets of the first and second flow chambers to the inlet of the detector and the connection of the other of the respective outlets of the first and second flow chambers to the inlet of the detector.

The control means provides that the gas flow through the first flow chamber alternates with the gas flow through the second flow chamber in a defined manner.

According to an aspect, the invention also relates to a measuring device as described above, wherein the measuring device comprises data processing means, which data processing means are configured for:

registering a first electrical sensing signal during the connection of said one of the respective outlets of the first and second flow chambers to the inlet of the detector, and registering a second electrical sensing signal during the connection of said other of the respective outlets of the first and second flow chambers to the inlet of the detector;

determining a difference signal from the first electrical sensing signal and the second electrical sensing signal, the difference signal corresponding to the difference of the concentration of the gas component in the first gas flow and the concentration of the gas component in the second gas flow.

The data processing means allow that data signals from the first gas flow can be compared with data signals from the second gas flow.

The adsorbent for moisture can comprise one or more of silica gel, activated charcoal, zeolites, and various carbohydrates. In an embodiment, saccharides are found to be very useful for the NO2 application. In the parallel version it can be adjusted in such a manner that the moist delayed characteristics resemble the reactant in the first chamber.

According to an aspect, the invention also relates to a measuring device as described above, wherein the absorbent for moisture is arranged in the second flow chamber.

In this embodiment, the adsorbent provides that the moisture concentration in the gas flow through the second flow chamber can be adjusted in such a manner that the moist delayed characteristics resemble the absorption by the reactant in the first flow chamber.

According to an aspect, the invention also relates to a measuring device as described above, wherein the adsorbent for moisture is arranged in the first and second flow chambers of the measuring device.

According to an aspect, the invention also relates to a measuring device as described above, wherein the control means are arranged for synchronized operation with the data processing means.

By synchronizing the operation of the control means with the operation of the data processing means a differential mode for the measuring device is facilitated.

According to an aspect, the invention also relates to a measuring device as described above, wherein the control means are provided with a timer.

The timer provides a timing for the control means to switch between the first gas flow and the second gas flow at predetermined time intervals.

According to an aspect, the invention also relates to a measuring device as described above, wherein the timer is arranged to cause at predetermined times the control means to control the selecting valve to connect either the outlet of the first flow chamber or the outlet of the second flow chamber to the inlet of the detector such that the respective flow chamber is in fluid communication with the detector.

By selecting the predetermined time larger than a dead time in the detector, accuracy of measurement is improved.

According to an aspect, the invention also relates to a measuring device as described above, wherein the outlet of the second flow chamber is connected to an outflow nozzle when the outlet of the first flow chamber is connected to the inlet of the detector.

According to an aspect, the invention also relates to a measuring device as described above, wherein the outlet of the first flow chamber is connected to an outflow nozzle when the outlet of the second flow chamber is connected to the inlet of the detector.

According to the invention both gas flows are continuously running, to avoid stagnant gas in either of the first and second chambers.

According to an aspect, the invention also relates to a measuring device as described above, wherein the selecting valve comprises a bi-stable four-way valve.

The use of a bi-stable four-way valve or a bi-stable valve with an equivalent function provides an actuation of the selecting valve which requires low power. Such an arrangement is beneficial in particular for remote applications driven by e.g. batteries or solar power.

According to an aspect, the invention also relates to a measuring device as described above, wherein the detector comprises an electrochemical cell configured for sensing one of a group of gas components selected from nitrogen dioxide, NO2; nitrogen monoxide, NO; carbon monoxide, CO; carbon dioxide, CO2; ozone, O3; hydrogen sulphide, H2S, sulphur dioxide SO2, and the reactant for the gas component is selected to absorb the respective gas component.

In case of NO2 as targeted gas component, triethanolamine (TEA) can be selected as reactant.

A candidate for CO separation is Cu(I)—Cl.

For NO detection the measuring device can be modified by providing an ozone generator that is arranged to add ozone to the gas as received by the flow generating device. NO will react with ozone to form NO2.

According to an aspect, the invention also relates to a method for measuring a level of a gas component in a gas comprising:

receiving a gas flow at an inlet and supplying the gas flow in a first part to a first flow chamber as a first gas flow and in a second part to second flow chamber as a second gas flow, in such a way that during use a first gas flow in the first flow chamber is parallel to a second gas flow in the second flow chamber;

absorbing the gas component in the first gas flow by providing an absorber substance for the gas component in the first flow chamber;

selecting one of the first gas flow from the first flow chamber and the second gas flow from the second flow chamber respectively as an inlet to a detector configured for sensing a level of the gas component in the gas and for generating an electrical sensing signal that corresponds with the level of the gas component in the respective gas flow;

providing an absorbent for moisture in the measuring device downstream of the first and second flow chambers in a flow chamber downstream from the selection of the first gas flow or the second gas flow and upstream from the detector, wherein the absorbent for moisture is not an absorber substance for the gas component, and the absorbent for moisture is arranged for dampening variation of moisture in the received gas flow.

According to an aspect, the invention also relates to a method as described above, comprising:

measuring a first electrical sensing signal during flow of the first gas flow through the detector and a second electrical sensing signal during flow of the second gas flow through the detector.

According to an aspect, the invention also relates to a method as described above, comprising establishing a difference signal from the first and the second electrical sensing signal wherein the difference signal corresponds with a difference between the concentration of the gas component in the first gas flow and the concentration of the gas component in the second gas flow.

According to an aspect, the invention also relates to a method as described above, comprising:

providing an adsorbent for moisture in the second flow chamber, wherein the adsorbent for moisture is not an reactant for the gas component.

According to an aspect, the invention also relates to a method as described above, wherein said selecting one of the first gas flow and the second gas flow from the first flow chamber and the second flow chamber respectively as an inlet to a detector is timer-controlled.

According to an aspect, the invention also relates to a method as described above, further comprising selecting the other of the first gas flow and the second gas flow from the first flow chamber and the second flow chamber respectively as an inlet to an outflow nozzle, when said one of the first gas flow and the second gas flow from the first flow chamber and the second flow chamber respectively is connected to the detector.

Advantageous embodiments are further defined by the dependent claims.

BRIEF DESCRIPTION OF DRAWINGS

The invention will be explained in more detail below with reference to drawings in which illustrative embodiments of the invention are shown. It will be appreciated by the person skilled in the art that other alternative and equivalent embodiments of the invention can be conceived and reduced to practice without departing from the true spirit of the invention, the scope of the invention being limited only by the appended claims.

DESCRIPTION OF EMBODIMENTS

Figure 1:
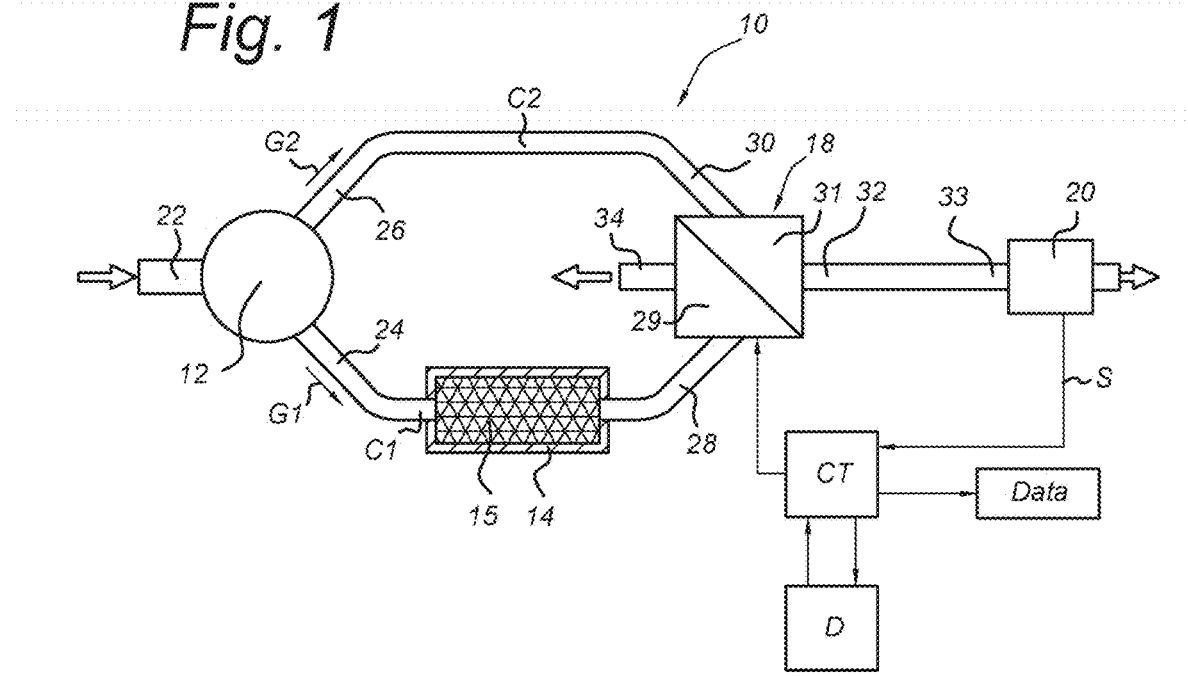
FIG. 1 shows schematically a measuring device according to an embodiment of the invention.

FIG. 1 shows schematically a measuring device 10 according to an embodiment of the invention. The measuring device comprises a flow generating device 12, a first conduit or first flow chamber C1, a second conduit or second flow chamber C2, a selecting valve 18 and an electrochemical detector 20.

The flow generating device 12 has an inlet 22 for receiving gas from a gas volume that may contain an amount of a polluting substance (hereafter: the targeted gas component) that is to be detected by the measuring device.

The flow generating device 12 which can comprise a fan or a gas pump is arranged to supply the received gas through a first outlet channel to an inlet 24 of the first conduit or first flow chamber C1 and through a second outlet channel to an inlet 26 of the second conduit or second flow chamber C2.

The flow generating device 12 may be embodied with a single outlet which is forked into two conduits that couple to a respective conduit or flow chamber C1; C2.

Alternatively the flow generating device 12 may have two outlets that couple to a respective conduit or flow chamber.

In an alternative embodiment, the measuring device may comprise a flow generating device coupled to the first conduit and a second flow generating device coupled to the second conduit, so as to have a separate inlet for each conduit.

In this manner the flow generating device 12 provides a first gas flow G1 in the first conduit C1, parallel to a second gas flow G2 in the second conduit C2.

The first conduit C1 has an outlet 28 that is connected to a first inlet 29 of a selecting valve 18. The second conduit C2 has an outlet 30 that is connected to a second inlet 31 of the selecting valve 18.

The selecting valve 18 comprises two outlets of which one outlet is connected to an outlet nozzle 34 and the other outlet 32 is connected to an inlet of a detector 20. The selecting valve 18 can be selected for connection of one of the first conduit C1 and the second conduit C2 to the inlet 33 of the detector, while the other of the conduits is switched by the selecting valve to have an open flow into ambient air through the outlet nozzle. In this manner the flows G1, G2 through the first conduit C1 and the second conduit C2 are continuous.

In an embodiment, the selecting valve 18 comprises a bi-stable four-way valve. A bi-stable valve requires relatively low power, which may provide an advantage for remote applications.

The detector 20 receives the gas flow selected by the selecting valve to sense the gas component concentration in the gas. The detector 20 generates an electrical sensing signal corresponding with the gas component concentration.

According to the invention, the first conduit c1 is provided with an reactant 15 for absorbing said gas component (i.e., an absorber substance for selectively absorbing said gas component). In this manner the targeted gas component is removed from the gas flow G1 through the first conduit C1.

In an embodiment, the reactant 15 is positioned in a cartridge 14 which can be accommodated in the first conduit C1.

The selecting valve 18 of the measuring device 10 alternately couples the first gas flow G1 from the first conduit C1, i.e., the gas flow without the targeted gas component, or the other or second gas flow G2 through the second conduit C2 which contains an amount of the targeted gas, to the detector 20.

Thus the detector 20 is alternately exposed to a gas flow with, G2, or without, G1, the targeted gas component. The other components in the gas flows G1, G2 will be substantially the same, since these components are not affected by the reactant 15.

Thus, the detector 20 will observe a variation of the sensing signal that varies with the switching frequency between the second gas flow G2 with the targeted gas component and the first gas flow G1 without the targeted component. As a result the variation of the sensing signal will be proportional with the presence of the targeted gas component.

By determining a differential signal between the sensing signal of the second gas flow G2 with the targeted gas component from the second conduit C2 and the sensing of the first gas flow G1 that passed the reactant 15 in the first conduit C1, thus substantially without the targeted gas component, the differential signal is proportional to the concentration of the targeted gas component in the ambient air as sampled by the flow generating device 12. Additionally, since the first and second gas flows G1, G2 only differ in the concentration of the targeted gas component, the detector 20 will sense a same base line for both first and second gas flows.

The targeted gas component may be nitrogen dioxide NO2, nitric oxide NOx, sulphur dioxide SO2, carbon monoxide CO carbon dioxide, CO2; ozone, O3; hydrogen sulphide, H2S or another gas species.

The reactant 15 is selected based on the targeted gas component. For NO2 the reactant 15 may comprise triethanolamine.

For CO detection, Cu(I)—Cl is a candidate material for absorption of this gas component.

For NO detection, the measuring device may comprise an ozone generator that produces an ozone flow that is added to the gas flow received by the flow generating device 12. Ozone will react with NO to form NO2 which can be detected as described above.

The measuring device 10 comprises a controller CT for controlling the selecting valve 18 to select which of the first and second gas flows G1, G2 is to pass through the detector 20. The controller CT may comprise a timer to determine the switching intervals of the selecting valve and the exposure time of the detector for each gas flow.

The detector CT is connected to a data processing means D, i.e. a processor coupled with a memory, the data processing means D being arranged for receiving the electrical sensing signal from the detector D. Additionally, the data processing means D are coupled or integrated with the controller CT to allow synchronization of the received electrical sensing signals with the respective first or second gas flow G1; G2 passing through the detector and determine the differential signal between the sensing signal from the first gas flow G1 and the sensing signal from the second gas flow G2.

The reactant 15 for the targeted gas component may also be an adsorbent for moisture. In that case, the moisture content of the first gas flow G1 which has been in contact with the reactant 15 for the targeted gas component, can differ from the moisture content of the second gas flow G2 which was not exposed to the reactant 15. As a result, the detector 20 would be alternately exposed to a first gas flow G1 substantially without moisture and a second gas flow G2 containing moisture. Since the function of detectors based on an electrochemical cell are typically sensitive to moisture, variation of moisture concentrations would interfere with the differential measurement of the targeted gas component.

Therefore, in an embodiment, the measuring device 10 comprises an adsorbent for moisture 16 which does not absorb or react or interact with the gas component. The adsorbent for moisture 16 is added to the volume of the measuring device 10 to prevent a difference in moisture content of the first gas flow G1 and the second gas flow G2.

In a further embodiment, the adsorbent for moisture 16 is arranged within the flow volume of the measuring device 10 upstream from the detector 20.

In this manner, removal of moisture upstream of the detector 20 reduces the uptake of moisture by electrochemical medium in the detector 20 and is thus beneficial for the operating conditions of the detector 20.

Figure 2:
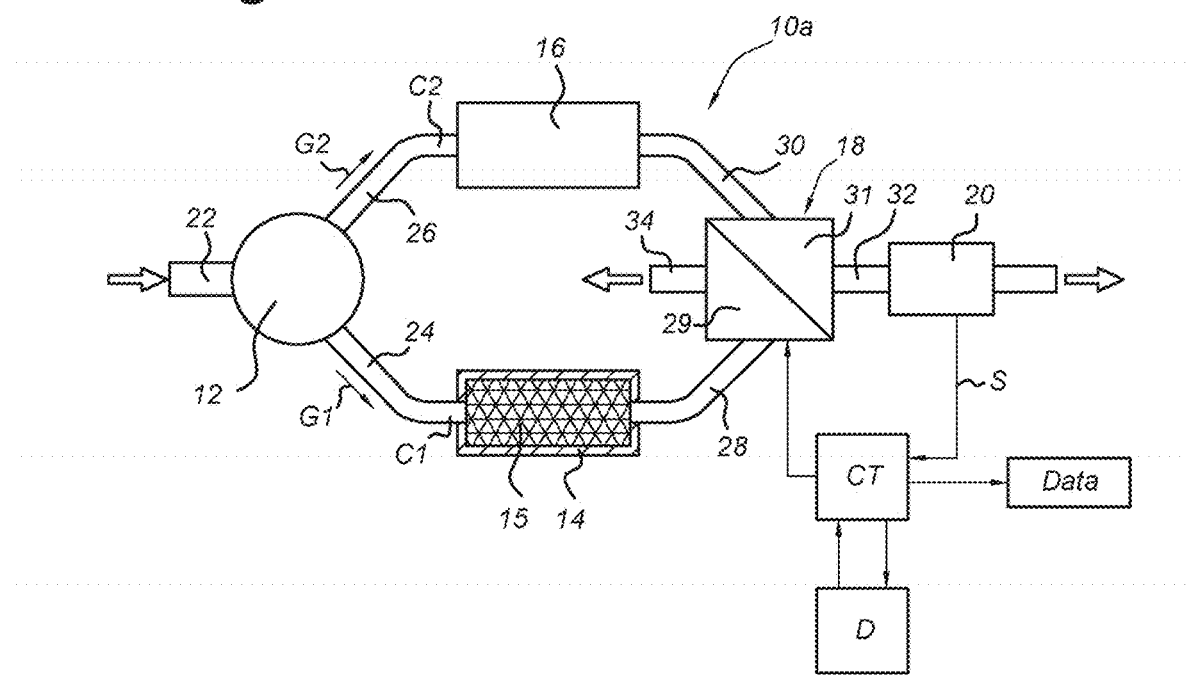
FIG. 2 shows schematically a measuring device according to an embodiment of the invention.

In an alternative further embodiment, the adsorbent for moisture 16 is arranged in the second conduit C2 of the measuring device 10A. See FIG. 2. In this embodiment, the adsorbent for moisture 16 is configured to absorb moisture from the second gas flow G2 so as to balance the low moisture concentration of the first gas flow G1, reduced by the reactant 15 for the targeted gas component.

In an alternative further embodiment, the measuring device 10 comprises in the first and second conduits C1, C2 an adsorbent for moisture 16 which does not absorb the gas component. In this case, the moisture is captured in each conduit C1, C2 to a similar degree by the adsorbent 16.

Figure 3:
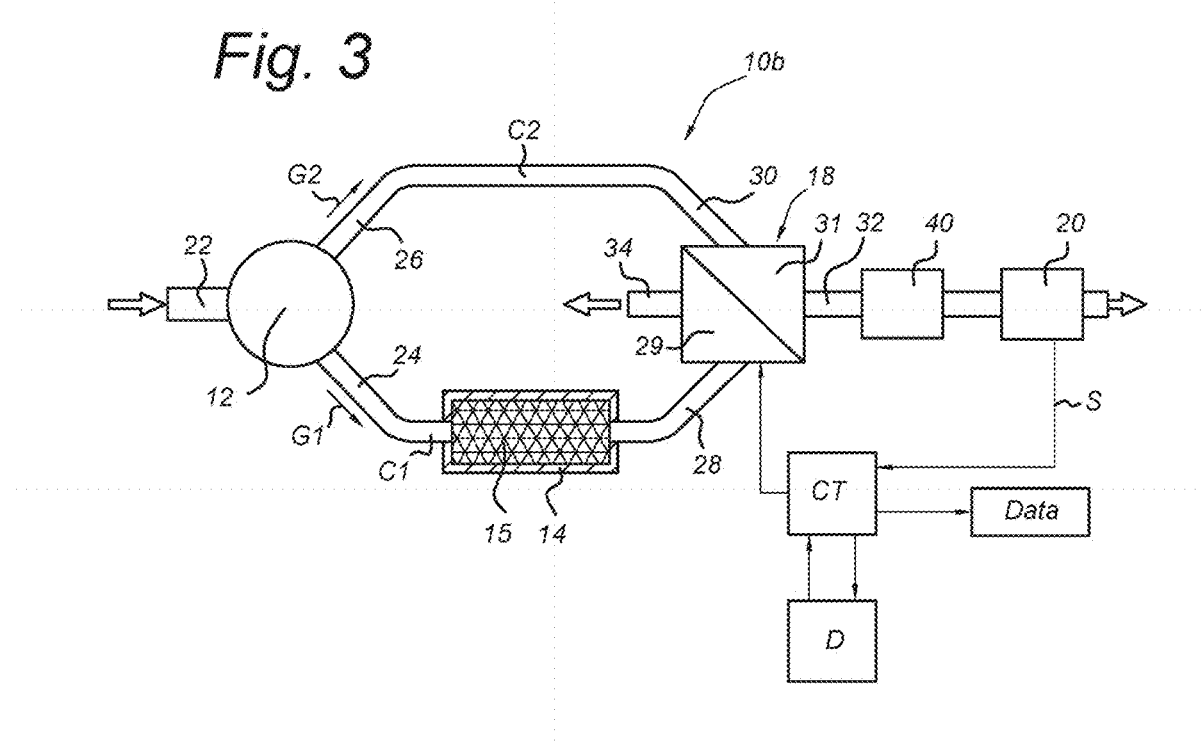
FIG. 3 shows schematically a measuring device according to an embodiment of the invention.

FIG. 3 shows a measuring device 10B according to an embodiment of the invention.

In this embodiment, the measuring device 10B comprises a chamber 40 containing an adsorbent for moisture which does not absorb the gas component, wherein the chamber 40 with the adsorbent for moisture is arranged downstream of the first and second conduits C1, C2 and upstream from the detector 20. In this arrangement the adsorbent for moisture optimally dampens variation of moisture in the gas taken in by the flow generating device 12. As shown in FIG. 3, the chamber 40 with the adsorbent for moisture is arranged downstream of the selecting valve 18 and upstream of the detector 20.

The adsorbent for moisture can comprise one or more of silica gel, activated charcoal, a zeolite, and a carbohydrate.

The measuring device 10, 10A, 10B can be used for measurement/detection of various gas components comprising nitrogen dioxide, NO2; nitrogen oxide, NOx; carbon monoxide, CO; sulphur dioxide, SO2 by selecting a detector 20 targeted to the respective gas component. The reactant 15 in the first conduit C1 is selected correspondingly as reactant 15 for said gas component.

Figure 4:
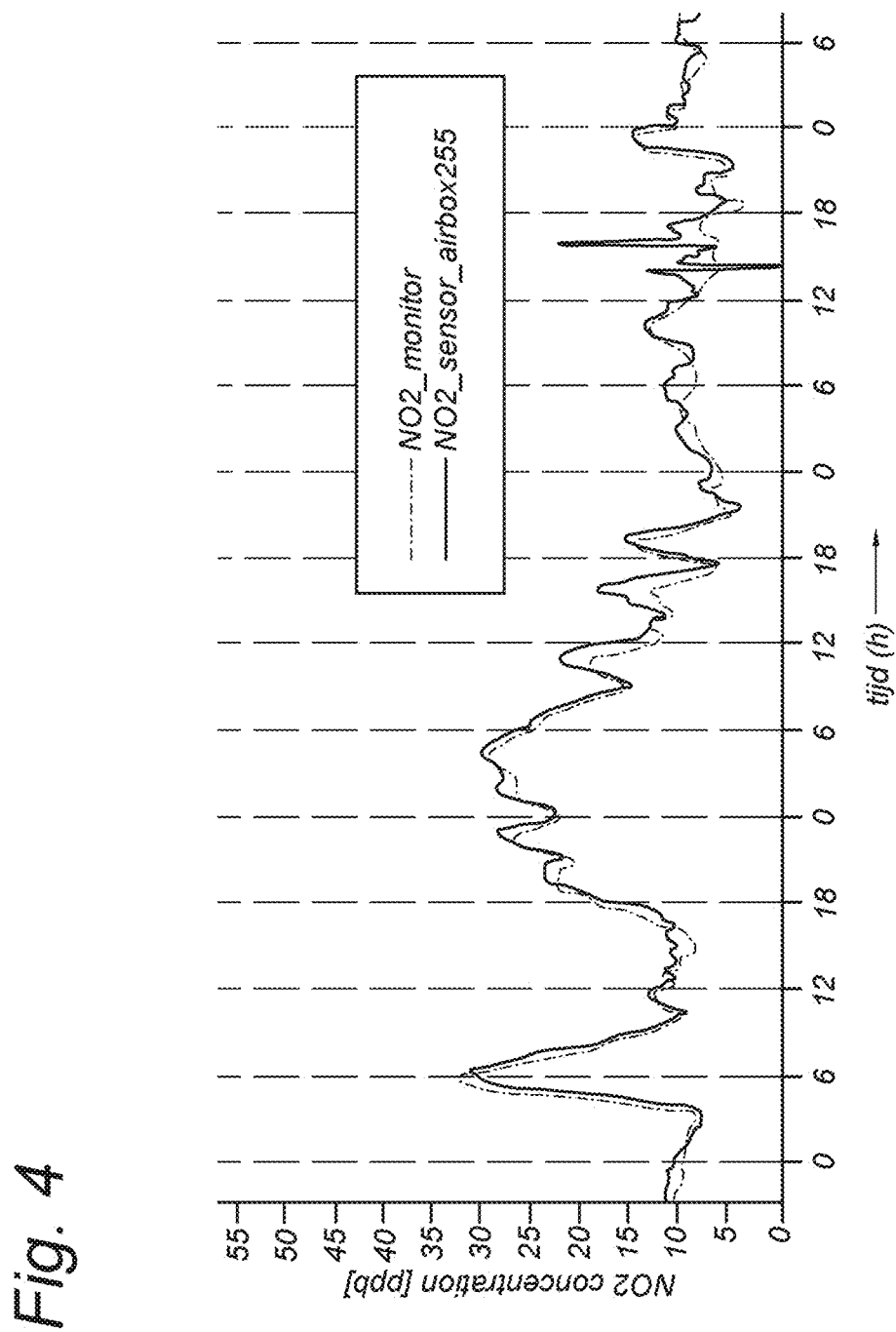
FIG. 4 shows a plot of a measurement of nitrogen dioxide in ambient air by the measuring device according to the invention, compared with a reference NO2 chemo luminescence monitor.

FIG. 4 shows an exemplary measurement of a concentration of nitrogen dioxide in ambient air done by a measuring device according to the invention.

In this plot an adsorbent for moisture, i.e. glucose, is arranged in the second conduit to obtain a gas flow in the second conduit with a similar moisture concentration as the gas flow in the first conduit. The switching frequency between the gas flow through the first conduit and through the second conduit was approx. 10 minutes. The gas flows were approx. 20 ml/min In the plot the differential signal is shown as function of time by the solid line. The dotted line shows a simultaneous measurement of the same ambient by means of a NO2 chemo luminescence monitor (indicated in FIG. 4 as NO2 monitor).

Comparison of the two data sets in the plot shows that the measured data sets largely correspond. The measuring device according to the invention achieves a level of accuracy in the order of ppb, without requiring complex correction procedures.

In an embodiment, the data processing means D are additionally arranged to measure temperature and humidity (moisture) at the electrochemical cell of the detector 20. The temperature and humidity values measured at the electrochemical cell can be used by the data processing means D for verification and/or corrections of the measuring device 10, 10A, 10B.

Other alternatives and equivalent embodiments of the present invention are conceivable within the idea of the invention, as will be clear to the person skilled in the art. It is intended that the invention be construed as including all such modifications and alterations insofar as they come within the scope of the appended claims.

The invention claimed is:

1. Measuring device for measuring a level of a gas component in a gas comprising a gas pump (12), a first conduit or flow chamber (C1), a second conduit or flow chamber (C2), a selecting valve (18) and an electrochemical detector (20) configured for sensing the gas component level in the gas and for generating an electrical sensing signal corresponding with the gas component level;
the gas pump (12) having an inlet for receiving gas;
the gas pump (12) being connected through a first outlet channel to an inlet of the first flow chamber (C1);
the gas pump (12) being connected through a second outlet channel to an inlet of the second flow chamber (C2), in such a manner that in use a first gas flow (G1) in the first flow chamber (C1) is parallel to a second gas flow (G2) in the second flow chamber (C2);
an outlet of the first flow chamber (C1) being connected to a first inlet of the selecting valve (18);
an outlet of the second flow chamber (C2) being connected to a second inlet of the selecting valve (18);
the selecting valve (18) being connected through an outlet to an inlet of the detector (20);
the selecting valve (18) being configured to alternately connect one of the respective outlets of the first and second flow chambers (C1;C2) to the inlet of the detector (20), in which the outlet of the second flow chamber is connected to an outflow nozzle when the outlet of the first flow chamber is connected to the inlet of the detector,
and the outlet of the first flow chamber is connected to the outflow nozzle when the outlet of the second flow chamber is connected to the inlet of the detector, such that both gas flows are continuously running
wherein the first flow chamber (C1) is provided with an absorber substance (15) for selectively absorbing said gas component, and
wherein the measuring device comprises an absorbent (16) for moisture which does not absorb the gas component, the absorbent (16) for moisture being arranged downstream of the first and second flow chambers (C1;C2) in a flow chamber (40) downstream from the selecting valve (18) and upstream from the detector (20) in the measuring device, wherein the absorbent (16) for moisture is a carbohydrate arranged for dampening variation of moisture in the gas which was taken in by the gas pump (12).

2. Measuring device according to claim 1, further comprising control means (CT) for control of the selecting valve (18) to switch between the connection of one of the respective outlets of the first and second flow chambers (C1;C2) to the inlet of the detector (20) and the connection of the other of the respective outlets of the first and second flow chambers (C1;C2) to the inlet of the detector (20).

3. Measuring device according to claim 2, wherein the control means (CT) are arranged for synchronized operation with a data processing means (D).

4. Measuring device according to claim 3, wherein the control means (CT) are provided with a timer.

5. Measuring device according to claim 2, wherein the control means (CT) are provided with a timer.

6. Measuring device according to claim 5, wherein the timer is arranged to trigger at predetermined times the control means (CT) to control the selecting valve (18) to connect either the outlet of the first flow chamber (C1) or the outlet of the second flow chamber (C2) to the inlet of the detector (20) such that the respective flow chamber is in fluid communication with the detector (20).

7. Measuring device according to claim 2, wherein the measuring device comprises data processing means (D), which data processing means are configured for:
registering a first electrical sensing signal during the connection of said one of the respective outlets of the first and second flow chambers (C1;C2) to the inlet of the detector (20), and registering a second electrical sensing signal during the connection of said other of the respective outlets of the first and second flow chambers (C1;C2) to the inlet of the detector (20);
determining a difference signal from the first electrical sensing signal and the second electrical sensing signal, the difference signal corresponding to the difference of the level of the gas component in the first gas flow (G1) and the level of the gas component in the second gas flow (G2).

8. Measuring device according to claim 1, wherein the measuring device comprises data processing means (D), which data processing means are configured for:
registering a first electrical sensing signal during the connection of said one of the respective outlets of the first and second flow chambers (C1;C2) to the inlet of the detector (20), and registering a second electrical sensing signal during the connection of said other of the respective outlets of the first and second flow chambers (C1;C2) to the inlet of the detector (20);
determining a difference signal from the first electrical sensing signal and the second electrical sensing signal, the difference signal corresponding to the difference of the level of the gas component in the first gas flow (G1) and the level of the gas component in the second gas flow (G2).

9. Measuring device according to claim 8, wherein the control means (CT) are arranged for synchronized operation with the data processing means (D).

10. Measuring device according to claim 8, wherein the control means (CT) are provided with a timer.

11. Measuring device according to claim 1, wherein the selecting valve (18) comprises a bi-stable four-way valve.

12. Measuring device according to claim 1, wherein the detector (20) comprises an electrochemical cell configured for sensing one of gas components selected from a group comprising nitrogen dioxide, NO2; nitrogen oxide, NOx;

carbon monoxide, CO; carbon dioxide CO2; ozone, O3; hydrogen sulfide, H2S; sulphur dioxide, SO2, and
wherein the absorber substance (15) for the gas component is selected to absorb the respective gas component.

13. Measuring device according to claim 1, wherein the absorbent (16) for moisture is arranged to delay moisture from the first and second gas flows.

14. Measuring device according to claim 1, wherein the absorbent (16) for moisture is selected from saccharides.

15. Method for measuring a level of a gas component in a gas comprising:
receiving (12) a gas flow at an inlet and supplying the gas flow in a first part to a first flow chamber (C1) as a first gas flow (G1) and in a second part to second flow chamber (C2) as a second gas flow (G2), in such a way that during use a first gas flow (G1) in the first flow chamber (C1) is parallel to a second gas flow (G2) in the second flow chamber (C2);
absorbing the gas component in the first gas flow (G1) by providing an absorber substance (15) for the gas component in the first flow chamber (C1);
selecting (18) one of the first gas flow (G1) from the first flow chamber (C1) and the second gas flow (G2) from the second flow chamber (C2) respectively as an inlet to a detector (20) configured for sensing a level of the gas component in the gas and for generating an electrical sensing signal that corresponds with the level of the gas component in the respective gas flow (G1;G2), in which the outlet of the second flow chamber is connected to an outflow nozzle when the outlet of the first flow chamber is connected to the inlet of the detector,
and the outlet of the first flow chamber is connected to an outflow nozzle when the outlet of the second flow chamber is connected to the inlet of the detector, such that both gas flows are continuously running;
providing an absorbent (16) for moisture in the measuring device downstream of the first and second flow chambers (C1;C2) in a flow chamber (40) downstream from the selection (18) of the first gas flow (G1) or the second gas flow (G2) and upstream from the detector (20), wherein the absorbent (16) for moisture is a carbohydrate, not an absorber substance for the gas component, and
the absorbent (16) for moisture is arranged for dampening variation of moisture in the received gas flow.

16. Method according to claim 15, comprising:
measuring a first electrical sensing signal during flow of the first gas flow (G1) through the detector (20),
and a second electrical sensing signal during flow of the second gas flow (G2) through the detector (20).

17. Method according to claim 16, comprising establishing a difference signal from the first and the second electrical sensing signal wherein the difference signal corresponds with a difference between the level of the gas component in the first gas flow (G1) and the level of the gas component in the second gas flow (G2).

18. Method according to claim 15, wherein said selecting one of the first gas flow (G1) from the first flow chamber (C1) and the second gas flow (G2) from the second flow chamber (C2) respectively as an input to the detector (20) is timer-controlled.

19. Method according to claim 15, further comprising delaying moisture from the first and second gas flows by the absorbent (16) for moisture.

20. Method according to claim 15, wherein the absorbent (16) for moisture is selected from saccharides.

* * * * *